United States Patent
Chen

(10) Patent No.: US 11,141,069 B2
(45) Date of Patent: Oct. 12, 2021

(54) METHOD FOR INCREASING ACCURACY OF MEASUREMENT OF BODY TEMPERATURE

(71) Applicant: Hetaida Technology Co., Ltd., Dongguan (CN)

(72) Inventor: Zhenguang Chen, Dongguan (CN)

(73) Assignee: HETAIDA TECHNOLOGY CO., LTD., Dongguan (CN)

( * ) Notice: Subject to any disclaimer, the term of this patent is extended or adjusted under 35 U.S.C. 154(b) by 332 days.

(21) Appl. No.: 16/260,139

(22) Filed: Jan. 29, 2019

(65) Prior Publication Data
US 2020/0237233 A1 Jul. 30, 2020

(51) Int. Cl.
G01K 15/00 (2006.01)
G01J 5/00 (2006.01)
G01K 1/00 (2006.01)
A61B 5/01 (2006.01)
G01J 5/02 (2006.01)
A61B 5/00 (2006.01)

(52) U.S. Cl.
CPC .............. *A61B 5/01* (2013.01); *A61B 5/0075* (2013.01); *G01J 5/0003* (2013.01); *G01J 5/0265* (2013.01); *A61B 5/0064* (2013.01)

(58) Field of Classification Search
USPC .............................. 374/1, 121, 142, 126, 128
See application file for complete search history.

(56) References Cited

U.S. PATENT DOCUMENTS

| | | | |
|---|---|---|---|
| 2004/0254472 A1* | 12/2004 | McQuilkin | A61B 5/015 600/473 |
| 2008/0045847 A1* | 2/2008 | Farag | A61B 5/02055 600/500 |
| 2016/0206211 A1* | 7/2016 | Naimi | G06T 7/0012 |

\* cited by examiner

*Primary Examiner* — Mirellys Jagan
(74) *Attorney, Agent, or Firm* — Leong C. Lei

(57) ABSTRACT

A method for increasing accuracy of measurement of body temperature includes a step of collecting an infrared signal to obtain an infrared signal value (step 1), a step of collecting a skin image to obtain a calibrating emissivity (step 2), a step of obtaining a calibrated infrared signal value according to the calibrating emissivity and the infrared signal value obtained in step 1 (step 3), and a step of making a conversion into an actual body temperature (step 4). Accordingly, an actual temperature value of the skin surface can be attained to increase the accuracy of measurement effectively, thereby allowing the measured result to be more close to the real body temperature of a tested target.

4 Claims, 1 Drawing Sheet

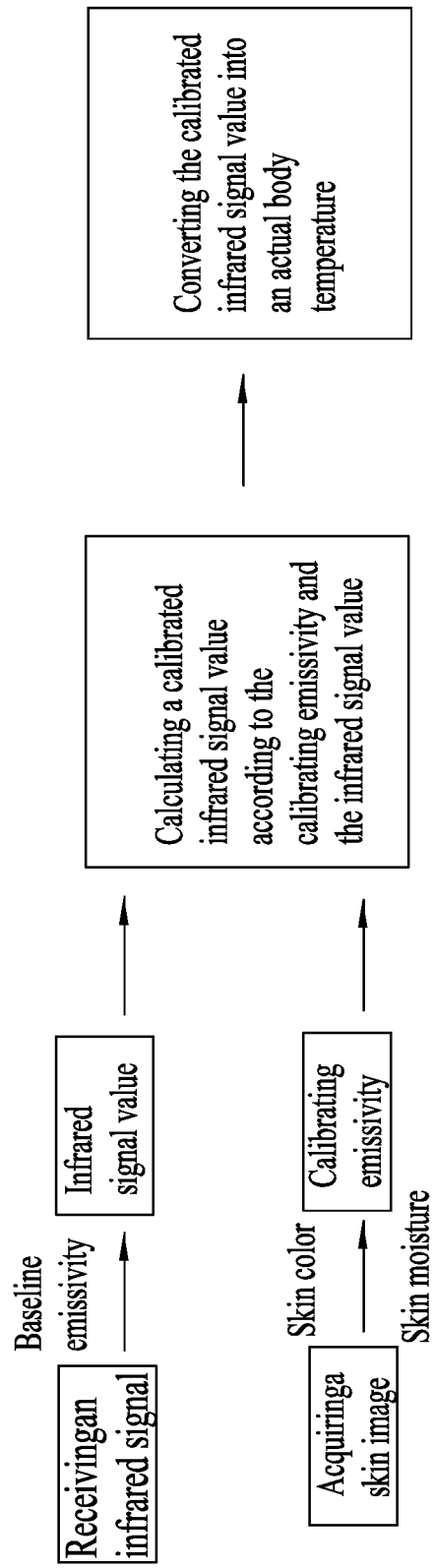

METHOD FOR INCREASING ACCURACY OF MEASUREMENT OF BODY TEMPERATURE

BACKGROUND OF THE INVENTION

1. Technical Field

The present invention relates to measurement of body temperature, and more particularly to a method for increasing accuracy of measurement of body temperature.

2. Description of Related Art

Generally, conventional infrared thermometers are adapted to people having various colors of skin. In fact, a black body is an idealized radiator capable of absorbing radiant energy of all wavelengths, and there is no reflected energy and no energy transmitted through the black body. The emissivity of the surface of the black body is 1. Almost all the objects in the natural world do not belong to the black body, and neither do human bodies. People in the world have different colors of skin, such as black, red, yellow and white, and the values of the emissivity for different colors of skin surface are different. It is common that the values of emissivity of human skin range from 0 to 1. Thus, when users having different skin colors are subjected to measurement of body temperature by conventional infrared thermometers, the inaccuracy of measurement is easily incurred.

Thereafter, some studies were invented to recognize the state of the skin according to information about images of a target site, such as the skin color. According to the obtained information, the original temperature tested by an infrared temperature sensor could be modified. This measurement takes account of different skin sites and skin states to a certain extent, but the accuracy of this measurement is still limited.

Therefore, the inventor has devised and herein discloses a novel technical scheme as described in the following paragraphs and as claimed in the appended claims.

SUMMARY OF THE INVENTION

In view of the shortcomings of the prior art, the objective of the present invention is to provide a method for increasing accuracy of measurement of body temperature which increases the accuracy of measuring the actual temperature at the skin surface effectively and gets a measured body temperature value which is very close to a real body temperature of a tested target.

To achieve the foregoing objective, the present invention implements the following technical scheme:

A method for increasing accuracy of measurement of body temperature includes:

step 1, a step of collecting an infrared signal. The step 1 is executed by receiving an infrared signal emitted by skin at a target site with an infrared temperature-measuring unit which is set at a predetermined baseline emissivity, thereby obtaining an infrared signal value;

step 2, a step of collecting a skin image. The step 2 is executed by acquiring an image of the skin at the target site, wherein the image of the skin at the target site has information which at least includes a skin color and a skin surface moisture, making analysis and calculation according to the skin color and the skin surface moisture to thereby obtain an emissivity of a surface of the skin at the target site and define the emissivity as a calibrating emissivity;

step 3, a step of calibrating the infrared signal. The step 3 is executed by making a calculation according to the calibrating emissivity and the infrared signal value obtained in step 1, thereby obtaining a calibrated infrared signal value; and step 4, a step of making a conversion into an actual body temperature. The step 4 is executed by converting the calibrated infrared signal value into an actual body temperature.

Preferably, the step of collecting the infrared signal and the step of collecting the skin image can be executed in sequence or in reverse order, or executed simultaneously.

Preferably, the baseline emissivity has a value greater than 0 and smaller than or equal to 1.

Preferably, in the step 2, the skin image is collected by a camera.

By comparison with the prior art, the present invention has obvious advantages and beneficial effects. In particular, according to the technical scheme described above, the disclosed method primarily uses the preset baseline emissivity to get the infrared signal value emitted by the skin at the target site, collects the skin image to calculate the calibrating emissivity, calculates according to both of the calibrating emissivity and the infrared signal value to obtain the calibrated infrared signal value, and then makes the conversion from the calibrated infrared signal value to the actual body temperature. Therefore, the method effectively enhances the accuracy of measurement, and the measured result is more close to a real temperature value of the skin surface of the tested target.

The structural features and advantages of the present invention over the prior art will become more apparent by reading following descriptions in conjunction with the corresponding drawings.

BRIEF DESCRIPTION OF THE DRAWING

FIG. 1 is a flow chart of a method of one embodiment of the present invention.

DETAILED DESCRIPTION OF THE PREFERRED EMBODIMENTS

FIG. 1 illustrates a flow chart of a preferred embodiment of the present invention.

As shown, a method for increasing accuracy of measurement of body temperature of the present invention includes following steps.

Step 1 is a step of collecting an infrared signal. In this step, an infrared signal emitted by skin at a target site is received by using an infrared temperature-measuring unit which is set at a predetermined baseline emissivity, thereby obtaining an infrared signal value. Preferably, the baseline emissivity can be an arbitrary value which is greater than 0 and smaller than or equal to 1.

Step 2 is a step of collecting a skin image. In this step, an image of the skin at the target site is acquired. The image of the skin at the target site has information which at least includes a skin color and a skin surface moisture. Then, according to the skin color and the skin surface moisture, an analysis and a calculation are made to obtain an emissivity of a surface of the skin at the target site and thence define the emissivity as a calibrating emissivity. Herein, the image of the skin is usually collected by using a camera.

Step 3 is a step of calibrating the infrared signal. In this step, it is executed by making a calculation according to the calibrating emissivity and the infrared signal value obtained in step 1 and thence obtaining a calibrated infrared signal value.

Step 4, a step of making a conversion into an actual body temperature. In this step, it is executed by converting the calibrated infrared signal value into an actual body temperature.

It is noted that the step of collecting the infrared signal and the step of collecting the skin image can be executed in sequence or in reverse order, or executed simultaneously.

The feature of the disclosed method is that the method mainly uses the preset baseline emissivity to get the infrared signal value emitted by the skin at the target site, collects the skin image to obtain the calibrating emissivity through calculation, calculates according to the calibrating emissivity and the infrared signal value to obtain the calibrated infrared signal value, and then makes the conversion from the calibrated infrared signal value to the actual body temperature. Therefore, the method effectively increases the accuracy of measurement, and the measured result is more close to a real temperature value of the skin surface of the tested target.

While the embodiment of the present invention is shown and described above, it is understood that the embodiment is not intended to limit the scope of the present invention. Moreover, it is understood that further detailed revisions, equivalent variations, and modifications may be made without departing from the scope of the present invention.

What is claimed is:

1. A method for increasing accuracy of measurement of body temperature, comprising:

step 1, a step of collecting an infrared signal, wherein said step 1 is executed by receiving an infrared signal emitted by skin at a target site with an infrared temperature-measuring unit which is set at a predetermined baseline emissivity, thereby obtaining an infrared signal value;

step 2, a step of collecting a skin image, wherein said step 2 is executed by acquiring an image of said skin at said target site, wherein said image of said skin at said target site has information which at least includes a skin color and a skin surface moisture, and making an analysis and calculation according to the skin color and the skin surface moisture to thereby obtain an emissivity of a surface of said skin at said target site and define said emissivity as a calibrating emissivity;

step 3, a step of calibrating the infrared signal, wherein said step 3 is executed by making a calculation according to said calibrating emissivity and said infrared signal value obtained in step 1 and thence obtaining a calibrated infrared signal value; and step 4, a step of making a conversion into an actual body temperature, wherein said step 4 is executed by converting said calibrated infrared signal value into an actual body temperature.

2. The method of claim 1, wherein the step of collecting the infrared signal and the step of collecting the skin image are executed in sequence or in reverse order, or executed simultaneously.

3. The method of claim 1, wherein the baseline emissivity has a value greater than 0 and smaller than or equal to 1.

4. The method of claim 1, wherein in step 2, said image of said skin is collected by a camera.

* * * * *